United States Patent [19]

Morgan, Jr.

[11] Patent Number: 5,376,356
[45] Date of Patent: Dec. 27, 1994

[54] IMAGING TISSUE SITES OF INFLAMMATION

[75] Inventor: A. Charles Morgan, Jr., Edmonds, Wash.

[73] Assignee: NeoRx Corporation, Seattle, Wash.

[21] Appl. No.: 726,894

[22] Filed: Jul. 8, 1991

Related U.S. Application Data

[63] Continuation of Ser. No. 324,285, Mar. 14, 1989, abandoned.

[51] Int. Cl.$^5$ .............................................. A61K 49/02
[52] U.S. Cl. ................... 424/1.41; 424/1.49; 424/1.53; 424/1.69
[58] Field of Search ................. 424/1.1, 85.91; 514/2; 530/388.1, 388.22, 388.23, 388.24, 388.73, 388.75, 391.3, 402, 403

[56] References Cited

U.S. PATENT DOCUMENTS

| | | | |
|---|---|---|---|
| 4,348,375 | 9/1982 | Goedmans | 424/1.1 |
| 4,427,660 | 1/1984 | Schiffman et al. | 424/177 |
| 4,672,044 | 6/1987 | Schreiber | 436/501 |
| 4,683,292 | 7/1987 | Hahn | 530/328 |
| 4,741,900 | 5/1988 | Alvarez et al. | 424/1.1 X |
| 4,772,584 | 9/1988 | Cleary et al. | 514/2 |
| 4,916,118 | 4/1990 | Fidler et al. | 514/16 |
| 4,917,878 | 4/1990 | Thakur | 424/1.1 |
| 4,926,869 | 5/1990 | Rubin et al. | 424/1.1 X |
| 5,110,738 | 5/1992 | Takano et al. | 435/240.27 |

FOREIGN PATENT DOCUMENTS 9013317 11/1990 WIPO .

*Primary Examiner*—Robert L. Stoll
*Assistant Examiner*—John M. Covert
*Attorney, Agent, or Firm*—Burns, Doane, Swecker & Mathis

[57] ABSTRACT

The present invention involves a method of imaging tissue sites of inflammation which takes advantage of the up-regulation of surface antigenic markers on leukocytes upon activation thereof. A recognition agent selected from the group of chemotactic peptides, eosinophilic peptides and agents which are capable of selective interaction with a chemotactic receptor associated with activated leukocytes is radiolabeled. The radiolabeled recognition agent is infused into a patient and the patient's tissue sites are thereafter imaged in order to detect, evaluate or monitor tissue damage mediated by inflammation.

6 Claims, No Drawings

IMAGING TISSUE SITES OF INFLAMMATION

This is a continuation of Ser. No. 07/324,285, filed Mar. 14, 1989, now abandoned.

BACKGROUND OF THE INVENTION

1. Technical Field of the Invention

The present invention relates to the field of diagnostic imaging. More specifically, the invention involves improved imaging of tissue sites of inflammation. Improved diagnostic images result from an increase in the number of labeled leukocytes in the area of the inflammation or from improved selectivity of antibodies or peptides for activated leukocytes in sites of inflammation versus non-activated leukocytes in the circulation.

2. Background Art

Inflammation occurs as a result of infection with a microorganism, tissue injury, or, as has been recently recognized, in non-apparent tissue injury associated with transient ischemia. A major application of imaging agents targeted to inflammation has been the imaging of abscesses due to regional replication of microorganisms.

Two general methodologies have been developed for imaging abscesses caused by replication of infectious organisms like bacteria or fungi. The first relies on detection of antigens expressed by the bacteria or fungi. In this case, antigen expressed by the microorganism itself is the target for imaging by antibody. The second method makes use of the fact that growth of infectious organisms will cause inflammation. The inflammation process then can be used as a target for imaging.

The most utilized method for imaging inflammation is one in which polymorphonuclear leukocytes (PMNs) or unfractionated leukocytes are isolated from a patient and labeled with radionuclides (for instance, with $^{111}$In). The labeled autologous leukocytes are then reinjected into the donor. A certain percentage of the labeled PMNs will accumulate at the sites of abscess formation or inflammation. However, many drawbacks have been experienced using this methodology. One such difficulty relates to the labeling methodologies and their effect on leukocyte trafficking. Oxidative processes used in the labeling procedure may cause the PMNs to be more effectively removed by the reticulo-endothelial system (RES) which has as its normal function the recognition, removal and destruction of effete cells in the body. Thus, in scans obtained by such labeling methodologies a substantial accumulation of labeled cells in the liver, spleen, and other RES sites is commonly observed. This RES accumulation detracts from a diagnostician's ability to detect inflammatory lesions within RES organs. Such accumulation also reduces the number of labeled cells that can accumulate at the site of the abscess (bioavailability), and thus decreases the sensitivity of inflammation detection in organs outside of the RES.

One abscess imaging methodology which has been suggested as an improvement involves a non-oxidative method of labeling the cells, making use of radiolabeled antibodies which bind to surface antigens of PMNs. Antibodies are labeled with a radioisotope suitable for imaging, and the antibody is then incubated with isolated PMNs or leukocytes prior to reinjection of the autologous cells into the donor. The method is an improvement because of its simplicity, but might also improve the number of leukocytes that can localize to abscesses because of reduced labeled cell accumulation in the RES system. Even with this improvement, only a small percentage of the labeled leukocytes will actually localize to the tissue sites of inflammation. Thus, there is a need for improved methods for enhancing accumulation of labeled leukocytes, and more specifically PMNs, into abscesses and sites of tissue inflammation.

Other potential methods for imaging abscesses or sites of inflammation use passively administered antibodies to localize to sites of inflammation. Such uses have been postulated for monoclonal antibodies directed to activation antigens expressed on monocytes which have matured into macrophages.

SUMMARY OF THE INVENTION

The present invention serves to improve upon diagnostic images described in the prior art by enhancing the amount of label associated with leukocytes accumulating at inflamed tissue sites, such as inflammatory lesions or abscesses. This enhancement of label at sites of tissue inflammation is achieved by infusing labeled recognition agents capable of interacting at the site of inflammation with leukocytes which have been activated during the inflammatory process. The labeled recognition agents exhibit an ability to traverse the vascular system and enter the tissue site to be imaged.

Enhanced label accumulation at the target tissue site may be accomplished in accordance with the present invention by paving the way for label through the bloodstream and peripheral tissue. That is, a non-labeled recognition agent is infused first to bind to these peripheral sites to permit more rapid and complete accumulation of later administered, labeled recognition agent at sites of inflammation.

The present invention encompasses imaging methods which employ as recognition agents monoclonal antibodies and peptides capable of interacting with receptors that have augmented expression on activated leukocytes. Monoclonal antibodies useful in the present invention are directed against epitopes of cell surface antigens which are up-regulated upon leukocyte activation. Thus, the monoclonal antibodies can interact with activated leukocytes located at sites of tissue inflammation. Monoclonal antibodies which are directed against activated leukocytes and do not exhibit substantial binding to non-activated leukocytes or exhibit a greater than 10-fold preference for activated leukocytes are especially useful recognition agents of the present invention.

Also, imaging methods which feature ex vivo activation of autologous leukocytes and incubation of these activated leukocytes with labeled recognition agent are contemplated by the present invention. Infusion of both the leukocytes and labeled recognition agent into a patient following incubation of the same serves to enhance the accumulation of label at tissue sites of inflammation.

DETAILED DESCRIPTION OF THE INVENTION

The primary function of polymorphonuclear leukocytes (PMNs) is the protection of a host against invasion by pathogenic organisms, such as bacteria or fungi. Other leukocytes, such as the monocyte, are additionally involved in this protective mechanism. Monocytes transformed into mononuclear phagocytes at the tissue site also participate in the protective process.

When pathogenic organisms become established in a host and begin proliferating, the infected host typically undergoes an inflammatory response. This inflammatory response is characterized by dilation of the blood vessels in the vicinity of the microorganism proliferation, increased vascular permeability in that area, and the movement of leukocytes, such as monocytes and PMNs, from the bloodstream into the infected tissue site. The increase in the volume of blood flowing past or through the area of infection; the increased ease of cellular passage through the blood vessel to the infected tissue; and the migration of phagocytic cells from the bloodstream to the infected area represent the host's response to the pathogenic organism's invasion.

PMNs and monocytes/mononuclear phagocytes which accumulate at a tissue site infected with such pathogenic organisms will provide an immune response through phagocytosis. That is, mononuclear phagocytes and PMNs will ingest the pathogenic cells and kill the ingested pathogens internally. Consequently, the greater the number of PMNs and mononuclear phagocytes that migrate to the infected area, the higher the rate of phagocytosis.

This migration of PMNs and mononuclear phagocytes to tissue sites that are inflamed also has ramifications for diagnostic imaging. By associating an imagable label with these mononuclear phagocytes and PMNs, an image of the infected area may be obtained. As with phagocytosis, the greater the number of PMNs and mononuclear phagocytes that migrate to the infected areas, the better the image.

The first aspect of the present invention involves a method of imaging tissue sites of inflammation comprising:

(1) labeling a recognition agent, wherein said agent is capable of interacting selectively with activated leukocytes accumulated at said tissue site;

(2) infusing labeled recognition agent into a patient; and (3) imaging said tissue sites, whereby medical conditions involving tissue damage mediated by inflammation may be detected, evaluated and monitored.

By imaging there is contemplated conventional diagnostic in vivo imaging. Briefly, a substance which is capable of detection within a patient, i.e., a labeled substance such as a radionuclide labeled antibody, is administered to a patient in an amount sufficient to deliver an adequate supply of labeled substance to the target tissue so as to permit an image to be generated. The radionuclide provides the imaging input, while the coupled (labeled) substance provides the targeting capability of the radiolabeled unit.

A tissue site of inflammation is one which exhibits tissue damage mediated by inflammation. Thus, a tissue site of inflammation may be one where damage to tissue prompts an inflammatory response. Alternatively, the damage to a tissue site may be exacerbated or be generated by an inflammatory response itself. In the first instance, a patient initially suffers tissue damage and then his immune system mounts an inflammatory response to that damage. In the second scenario, the inflammatory response induced by transient ischemia, for example, causes or exacerbates the tissue damage.

Exemplary of tissue damage mediated by inflammation are infectious agent multiplication and tissue abscesses. When infectious agents are involved, tissue damage may result from actions of the proliferating invader cells (the first situation described above) or from the inflammatory response (the second situation described above). By infectious agent, there is contemplated any pathogenic organism. Exemplary of such organisms are bacteria, viruses and fungi. Another example of tissue damage mediated by inflammation is the damage suffered by ischemic heart muscle brought about by myocardial infarction, since transient decreases in blood flow to tissue sites result in minimal tissue damage which, however, is sufficient to induce leukocyte activation and subsequent inflammation.

The labeling of the present invention may be accomplished by covalently or noncovalently linking a moiety which generates an input for an imaging technique with a recognition agent. The label-recognition agent conjugate will be administered to the patient. Exemplary of labels useful in the present invention are radionuclides. This labeling may be done by conventional techniques. For example, Alvarez et al. suggest methodologies for such labeling in U.S. Pat. No. 4,741,900.

Radionuclides useful within the present invention include gamma-emitters, positron-emitters and fluorescence emitters. Exemplary radionuclides are well-known in the art and include $^{111}$In, $^{198}$Au $^{113}$Ag, $^{111}$Ag, $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{109}$Pd, $^{105}$Rh, $^{128}$Ba, $^{197}$Hg, $^{203}$Pb, $^{212}$Pb, $^{67}$Ga, $^{68}$Ga, $^{64}$Cu, $^{67}$Cu, $^{97}$Ru, $^{75}$Br, $^{76}$Br, $^{77}$Br, $^{99m}$Tc, $^{11}$C, $^{13}$N, $^{15}$O and $^{18}$F.

The present invention also contemplates radionuclide labeling of a recognition agent via a chelating compound. A chelating compound is a moiety capable of complexing with a radionuclide. Exemplary chelating compounds are those described in published European Patent Applications numbers 0188256, 0289187 and 0203764.

Exemplary chelating compounds include compounds containing various combinations of nitrogen and sulfur atoms which act as the donor atoms for binding a metal or metal oxide. European Patent Application 0188256 discloses representative chelating compounds and their synthesis. A chelating compound within the present invention may be a compound having four to six nitrogen and sulfur donor atoms. One example of a chelating compound containing two nitrogens and two sulfurs is referred to herein as "$N_2S_2$". Other chelating compounds included within the invention have different numbers of nitrogen and sulfur atoms. Examples of these chelating compounds are identified in like manner herein as "$N_3S$", "$N_2S_3$", "$N_2S_4$" and "$N_3S_3$". Each of these representative chelating compounds is described in more detail below. In addition, the following U.S. patent applications are hereby incorporated in their entirety by reference: U.S. Ser. No. 065,017 (filed Jun. 19, 1987 currently pending) "Metal Radionuclide Labeled Proteins For Diagnosis And Therapy"; U.S. Ser. No. 172,004 (filed Mar. 23, 1988 U.S. Pat. No. 4,965,392), "Metal-Radionuclide-Labeled Proteins And Glycoproteins For Diagnosis And Therapy"; U.S. Ser. No. 201,134 (filed May 31, 1988 U.S. Pat. No. 4,965,496) "Metal Radionuclide Chelating Compounds For Improved Chelation Kinetics"; and U.S. Ser. No. 157,284 (filed Feb. 17, 1988 currently pending) "Anchimeric Radiometal Chelating Compounds."

The $N_2S_2$ metal chelating compounds may be dithio, diamino, diamidocarboxylic acids; amino/thio/amido combinations or derivatives thereof, e.g., a N,N'-bis-mercaptoacetyl, diamino carboxylic acid; esters capable of forming an amide bond in an aqueous medium; and intermediates of these esters. An example of an $N_2S_2$ metal chelating compounds has the following formula:

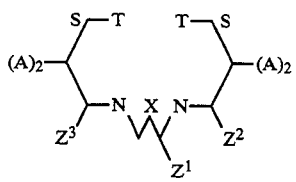

wherein:

one of $Z^1$, $Z^2$, $Z^3$ or $Z^4$ is RCW-(HNV)$_n$Y and the others are =O or H$_2$;

R is a divalent organic radical of at least 1 carbon atom and typically not more than 10, usually not more than 6 carbon atoms, usually from 1 to 3 carbon atoms, having from 0 to 2 heteroatoms which are chalcogen (O, S) or nitrogen, and is aliphatic, alicyclic, aromatic or heterocyclic (preferably aliphatic having from 0 to 2, usually 0 to 1 site of aliphatic unsaturation, e.g., ethylenic, and containing 1 to 2 carbon atoms);

W is oxygen or imino (=O or =NH), with the proviso that when Y is —NH$_2$ or —NHNH$_2$, the W bonded to the carbon atom bonded to Y is H$_2$;

V is RCW, where the two RCW groups may be the same or different, usually being of from 1 to 8, more usually of from 1 to 6 carbon atoms, preferably of from 2 to 3 carbon atoms;

n is 0 or 1;

T is an acyl or acylthio radical of from 2 to 10, usually 2-8 carbon atoms, either a hydrocarbyl acyl or substituted acylradical, usually aryl (e.g., phenyl) or alkyl (e.g., methyl); an organic sulfhydryl radical of from 1 to 10 carbon atoms, either substituted or unsubstituted hydrocarbyl; a heterocycle, particularly a chalcogen (O, S) heterocycle; an acylamidomethylene, where the acyl group is as defined above; hydrogen; sulfonato; an alkali metal ion; or the two T's may be taken together to define a polyvalent metal radionuclide, as the metal ion or metal ion oxide;

Substituents include nitro, cyano, halo, non-oxocarbonyl, carboxylic acid, amide and ester, and the like;

Y is a chemically reactive moiety capable of reacting with a recognition agent to bind the chelate thereto as is defined below;

A's are the same or different and are hydrogen, carboxylate or lower alkyl of from 1 to 6 carbon atoms, usually of from 1 to 3 carbon atoms, particularly methyl, or hydrogen; and X is a bond, methylene or CHZ$^4$.

A preferred group of N$_2$S$_2$ compounds will have one of the following formulae:

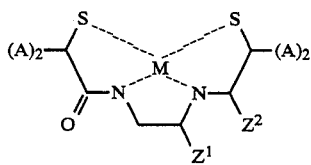

or

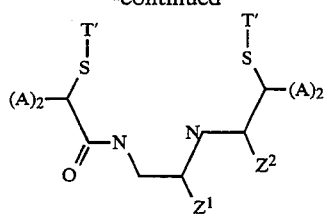

wherein all of the symbols are as defined previously except for M and T', and wherein:

M is a radionuclide capable of being chelated as the metal ion or metal ion oxide; and T' is a sulfur protective group, which includes acyl, acylthio, hydrocarbylthio or substituted-hydrocarbylthio or heterocyclicthio, where the acyl and hydrocarbyl groups may be aliphatic, alicyclic, aromatic or combinations thereof and the acyl group further includes heterocyclic, wherein acyl is normally carboxyacyl; T' will generally be of from 2 to 10 carbon atoms, usually 2 to 8 carbon atoms when acyl, where substituents will include non-oxo-carbonyl, halo, particularly fluoro and chloro, cyano and nitro.

N$_2$S$_2$-type chelate compounds will for the most part have the following formula:

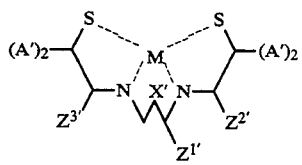

wherein:

one of $Z^{1'}$, $Z^{2'}$, $Z^{2'}$, $Z^{3'}$ or $Z^{4'}$ is R'CW' (HNV')$_{n'}$Y', and the others are =O or H$_2$;

(A')'s are the same or different and are hydrogen, carboxylate or lower alkyl of from 1 to 6, usually 1 to 3 carbon atoms, particularly methyl, usually hydrogen;

n' is 0 or 1;

V' is R'CW', where the (R'CW)'s may be the same or different, usually being of from 1 to 8, more usually of from 1 to 6 carbon atoms, preferably of from 2 to 3 carbon atoms;

W' is oxygen or imino (=N or =O), with the proviso that when Y' is —NH$_2$ or —NHNH$_2$, the W' bonded to the carbon atom bonded to Y' is H$_2$;

M is a radionuclide capable of being chelated as the metal ion or metal ion oxide;

X' is a bond, methylene or CHZ$^4$;

R' is an aliphatic divalent radical of from 1 to 6, usually from 1 to 3 carbon atoms, having from 0 to 1 site of aliphatic unsaturation and 0 to 2 heteroatoms, usually straight chain and preferably methylene or polymethylene of from 2 to 3 carbon atoms; and Y' is a chemically reactive moiety capable of reacting with a recognition agent to bind the chelate thereto as defined below.

The dashed lines in the formulae presented for the chelate compounds of the invention represent four coordinate covalent bonds between the metal radionuclide M and each of the two sulfur and the two nitrogen atoms shown in the formulae. Thus, the metal radionuclide is bound through relatively stable bonds in the chelate compounds of the invention.

An exemplary N$_2$S$_2$ conjugate is as depicted below:

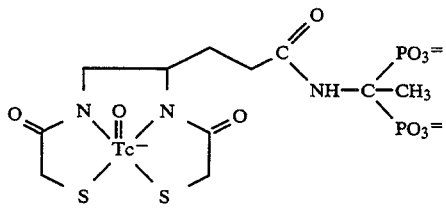

N₃S metal chelating compounds will have, for the most part, the following formula:

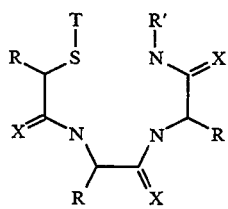

wherein:

T is H or a sulfur protecting group;

each X independently represents H₂ or O;

each R independently represents a substituent selected from the group consisting of hydrogen; alkyl; carboxylate; sulfonate; geminal dialkyl; a non-alkyl side chain of an amino acid other than cysteine (alkyl side chains being covered when R is an alkyl group); and —(CH₂)$_n$—Z;

Z represents a chemically reactive moiety capable of reacting with a recognition agent and binding the chelate thereto;

n is an integer of from 1 to about 4; and

R' is H₂; —(CH₂)$_n$—Z; or an alkyl group having one or more polar groups substituted thereon;

wherein the compound comprises at least one —(CH₂)$_n$—Z substituent.

When Z is —NH₂, n should be at least 2. When Z is other than —COOH, n preferably is 3.

The sulfur protecting group may be selected from alkyl, aryl, acyl (preferably alkanoyl or benzoyl), thioacyl groups having 1 to about 7 carbons, and organothio groups having 1 to about 10 carbons.

For the R groups, the alkyl groups generally contain from 1 to 7 carbons, preferably from 1 to 4 carbons, and most preferably represent methyl.

An exemplary N₃S conjugate is depicted below:

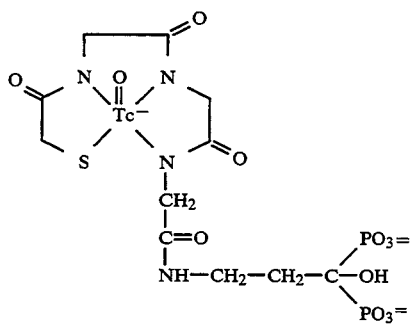

The N₂S₃ and N₂S₄ chelating compounds have the following formula:

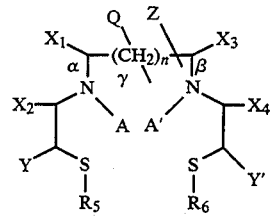

Examples of specific embodiments of the elements include the following:

X₁ and X₂ may be H or an oxy group (=O), but both are not =O. Likewise, X₃ and X₄ may be H or =O, but both are not =O. By selecting =O for X₁ or X₂, the N interposed between the carbons to which X₁ and X₂ are bonded will be an amide. Likewise, by selecting =O for X₃ or X₄, the N interposed between the carbons to which X₃ and X₄ are bonded will be an amide. Thus, a compound with zero, one or two amides may be formed by the appropriate selection of X₁, X₂, X₃ and X₄. Amide nitrogens, relative to amine nitrogens, afford greater stability to the complex formed with a metal, but at the expense of a diminished acceleration of complex formation. Thus, by selection of X₁, X₂, X₃ and X₄, compounds with a wide variety of chelating properties may be formed.

A is hydrogen (H), alkyl group of C₆ or less, —CH₂—CH₂—S—R₁ or —CO—CH₂—S—R₁, except when either X₁ or X₂ is =O, A is H. Similarly, A' is H, alkyl group of C₆ or less, —CH₂—CH₂—S—R₂ or —CO—CH₂—S—R₂, except when either X₃ or X₄ is =O, A' is H.

Y is —CH₂—S—R₃, or H, when A is H or an alkyl group of C₆ or less and A' is H or an alkyl group of C₆ or less. Alternatively, when either A or A' or both are not H or an alkyl group of C₆ or less, then Y is H. Similarly, Y' is —CH₂—S—R₄, or H, when A is H or an alkyl group of C₆ or less and A' is H or an alkyl group of C₆ or less. Alternatively, when either A or A' or both are not H or an alkyl group of C₆ or less, then Y is H. However, Y and Y' are both not H when A is H or an alkyl group of C₆ or less and A' is H or an alkyl group of C₆ or less. Thus, compounds of the formula depicted above may be formed containing two nitrogens and three or four sulfurs ("N₂S₃" and "N₂S₄", respectively). For "N₂S₄" compounds, two of the sulfurs are the sulfurs bearing R₅ and R₆ and the remaining two sulfurs are from A and A' or Y and Y'. The following formulae depict examples of N₂S₄ compounds in which two sulfurs are from Y and Y' (A) or in which two sulfurs are from A and A' (B).

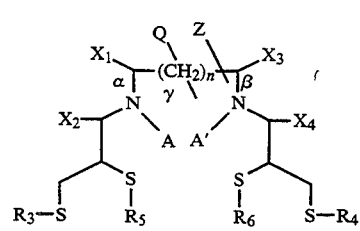

-continued

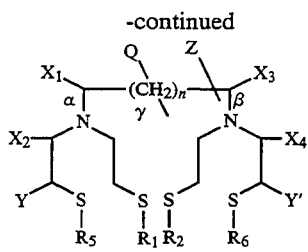

B $R_1$, $R_2$, $R_3$, $R_4$, $R_5$ and $R_6$ are independently selected from sulfur protecting groups. Groups which may be used include any of the alkyl, acyl and aryl groups, disulfides and bunte salts known by those skilled in the art.

Preferred groups are those that result in the formation of a thioacetal, hemithioacetal, thioester or acetamidomethyl substituent. Particularly preferred groups include p-anisylidine, acetonyl, tetrahydrylfuramyl, ethoxyethyl, tetrahydrylpyranyl, acetamidomethyl and derivatives thereof. When conjugated to a recognition agent, the protecting groups may be removed and left as sulfhydryls, either during storage or just prior to radiolabeling.

Q may be H or a polar group. One function of a polar group is to increase the hydrophilicity of the compound, e.g., to increase its aqueous solubility. Groups which may be used include carboxylates, sulfonates and secondary alcohols. A preferred group is —CH$_2$—COOH. Q may be attached to one of the positions designated as $\alpha$, $\beta$, and gamma. Because the number of methylene carbons at the gamma position is defined by n, which may be greater than one, the gamma position includes additional points for attachment of Q.

The distance by which the nitrogen atoms are separated may be increased by interposing methylene (—CH$_2$—) groups between the carbons bonded to the nitrogens. When the number of —CH$_2$— groups, represented by n, is greater than zero, then the number of carbon atoms separating the nitrogen atoms in compound I is increased accordingly. Preferred integers for n are 0 to 2.

Z is —(W)$_m$—R'. W is a group that functions as a "spacer arm" and may be useful to distance R' from the chelating portion of the compound. Groups which may be used include methylene (—CH$_2$—), methyleneoxy (—CH$_2$—O—), methylenecarbonyl (—CH$_2$—CO—), or combinations thereof. The number, m, of groups such as these would be typically 0 to about 30 and preferably 0 to about 5.

Z, or R' when m is 0, may be attached to one of the positions designated as $\alpha$, $\beta$, and gamma. Because the number of methylene carbons at the gamma position is defined by n, which may be greater than one, the gamma position includes additional points for attachment of a Z or an R'.

R' is a chemically reactive moiety capable of reacting with a recognition agent and binding the chelate thereto.

N$_3$S$_3$ compounds which contain three nitrogens and three sulfurs, have the following formula:

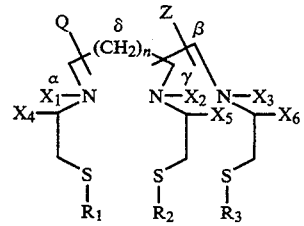

Examples of specific embodiments of the elements include the following.

$R_1$, $R_2$, and $R_3$ are independently selected from sulfur protecting groups. Groups which may be used include any of the alkyl, acyl, aryl groups, disulfides and bunte salts known by those skilled in the art. Preferred groups are those that result in an acyl, a thioacetal or a hemithioacetal. Particularly preferred groups include thioesters, p-anisylidine, acetonyl, tetrahydrylfuranyl, ethoxyethyl, tetrahydrylpyranyl, acetamidomethyl, and derivatives thereof.

$X_1$ and $X_2$ are independently selected from hydrogen and an alkyl group of $C_6$ or less. $X_3$ is H, an alkyl group of $C_6$ or less, or Z. $X_4$, $X_5$, and $X_6$ are independently selected from H and =O. The selection of =O results in the presence of an amide. Thus, a compound with zero, one, two or three amides may be formed by the appropriate selection of $X_4$, $X_5$, and $X_6$. Amide nitrogens, relative to amine nitrogens, afford greater stability to the complex formed with a metal, but at the expense of a diminished acceleration of complex formation. Thus, by selection of $X_4$, $X_5$, and $X_6$, compounds with a wide variety of chelating properties may be formed.

Q may be H or a polar group. One function of a polar group is to increase the hydrophilicity of the compound, e.g., to increase it aqueous solubility. Groups which may be used include carboxylates, sulfonates and secondary alcohols. A preferred group is —CH$_2$—COOH. Q may be attached to one of the positions designated as $\alpha$, $\beta$, gamma, and $\delta$. Because the number of methylene carbons at the $\delta$ position is defined by n, which may be greater than one, the $\delta$ position includes additional points for attachment of Q.

The distance by which the nitrogen atoms are separated may be increased by interposing methylene (—CH$_2$—) groups between the carbons bonded to the nitrogens. When the number of —CH$_2$— groups, represented by n, is greater than zero, then the number of carbon atoms separating the nitrogen atoms in compound II is increased accordingly. Preferred integers for n are 0 to 4.

Z is —(W)$_m$—R'. W is a group that functions as a "spacer arm" and may be useful to distance R' from the chelating portion of the compound. Groups which may be used include methylene (—CH$_2$—), methyleneoxy (—CH$_2$—O—), methylenecarbonyl (—CH$_2$—CO—), or combinations thereof. The number, m, of groups such as these would be typically 0 to about 30 and preferably 0 to about 5.

Z, or R' when m is 0, may be attached to $X_3$ or to one of the positions designated as $\alpha$, $\beta$, gamma, and $\delta$. Because the number of methylene carbons at the $\delta$ position is defined by n, which may be greater than one, the $\delta$ position includes additional points for attachment of a Z or an R'.

R' is a chemically reactive group capable of reacting with a recognition agent and binding the chelate thereto.

In $N_3S_3$ compounds, the carbon designated as $\beta$ may be bonded to any one of the carbons designated as $\alpha$, gamma and $\delta$. The following formulae depict compounds in which the $\beta$ carbon is bonded to the gamma carbon (A) and the $\beta$ carbon is bonded to the $\delta$ carbon (B).

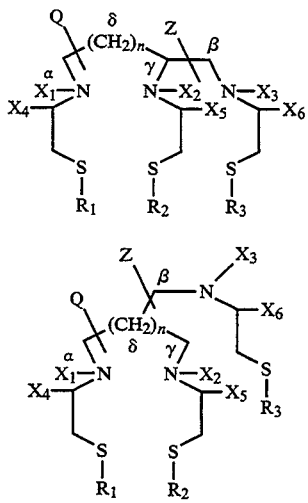

The chelating compounds of the present invention containing four to six donor sulfur and nitrogen atoms may be obtained in a manner described in European Patent Application Publication No. 0188256.

In the context of the present invention, the term "chemically reactive group" refers to a functional moiety capable of reacting with a recognition agent and thereby binding the chelate to that recognition agent. This chemically reactive group may be strongly electrophilic or nucleophilic, and thereby be available for reacting directly with a recognition agent. Alternatively, the moiety may be a weaker electrophile or nucleophile, and therefore require activation prior to binding with a recognition agent. This alternative would be desirable where it is necessary to delay activation of the chemically reactive moiety until a compound has been formed.

In either scenario, the chemically reactive moiety designated by various Letter symbols in the formulae is, indeed, chemically reactive. The scenarios differ by whether, following formation of a compound, the chemically reactive group is sufficiently reactive to be reacted directly with a recognition agent, or is activated first with one or more chemicals to render the group capable of reaction with a recognition agent. Illustrative chemically reactive groups and reactions thereof are described below.

Three methods are provided for producing the chelate-recognition conjugate useful in the method of the present invention. The first method features binding of the recognition agent to a radiolabeled compound, e.g., after a radiometal or radiometal oxide has been added to a chelating compound. A second method involves binding of the recognition agent to a fully formed, yet unlabeled, chelating compound, e.g., prior to the addition of a radiometal or radiometal oxide to the chelating compound. In both instances, the recognition agent is bound to the chelating compound via a chemically reactive group.

The step of combining a recognition agent with a labeled or unlabeled compound may be performed by direct reaction of the recognition agent with a chemically reactive moiety. This combination can also be achieved by "direct" reaction of a pre-activated chemically reactive moiety, as described above with a recognition agent. Alternatively, it may be desirable to include a preparatory step prior to the combining step to enhance the binding capability of the recognition agent. Such modification of the recognition agent may include reaction with any of the numerous bifunctional reagents reported in the literature.

A direct reaction involving a chelating compound and a modified or unmodified recognition agent requires a chemically reactive moiety capable of reacting with the modified or unmodified recognition agent. Exemplary chemically reactive moieties useful in the present invention include an alkyl group containing a good leaving group such as a halide, or a carbonyl-containing group such as an anhydride, an acid halide or an "active ester".

By an "active ester", there is contemplated esters that are highly reactive in nucleophilic substitution reactions. In the present invention, the modified or unmodified recognition agent would serve as the nucleophile. Typically, the esters will be activated phenols and cyclic compounds based upon hydroxylamine. Examples of commonly used "active" ester groups are tetrafluorophenyl, N-succinimidyl, nitrophenyl, isothiocyanate and substituted isothiocyanates. Alternatively, a chemically reactive moiety may serve as the nucleophile, such as an amino or sulfhydryl group capable of reacting with a modified recognition agent, e.g., a recognition agent containing a maleimide moiety.

Another preparatory step optionally used in the practice of the present invention is the activation of the chemically reactive moiety to enhance reactivity of the chelating compound with the recognition agent, as referred to above. Exemplary of such an activation is the conversion of a carboxyl moiety into an active ester. Another example is the activation of a chemical reactive moiety protected by a protective group. Removal of the protective group constitutes an activation. For example, removal of a phenylsulfonyl protective group from a succinimide derivative results in the conversion of the succinimide moiety into a maleimide moiety, which is highly reactive in nucleophilic addition reactions. Activation of the chemically reactive moiety also includes reaction of a nucleophilic moiety on the chelating compound with a bifunctional reagent. It will be evident to one skilled in the art that a variety of homobifunctional and heterobifunctional agents may be employed within the present invention to achieve such activation.

A third method for providing a radiolabeled recognition agent using a chelating compound bridge incorporates into the recognition agent a compound that is suitable for radiolabeling during the synthesis of such a compound. That is, a recognition agent is covalently attached to a precursor of a compound suitable for radiolabeling. Following this covalent attachment, the synthesis of the precursor compound is completed, such that the resultant chelating compound-recognition agent complex is suitable for radiolabeling.

As a recognition agent useful in the present invention, there is contemplated a monoclonal antibody or fragment thereof directed against a leukocyte activation marker. A leukocyte activation marker is a cell surface antigen which is poorly expressed or not expressed at all on leukocytes until the leukocyte is activated or caused to differentiate.

Activation of leukocytes, such as PMNs and monocytes, and their migration to sites of inflammation appear to take place in vivo as a result of an inflammatory response. Granulocyte activation may also be induced ex vivo by treatment with activators, such as granulocyte-macrophage colony stimulating factor (GM-CSF), granulocyte colony stimulating factor (G-CSF), gamma interferon, a calcium ionophore or by other agents capable of inducing an oxidative burst. Similarly, monocytes can be activated with gamma-interferon, monocyte colony stimulating factor (M-CSF), colony stimulating factor-1 (CSF-1) or tumor necrosis factor (TNF). Natural killer (NK) cells can be activated with alpha or gamma-interferon and interleukin-2, and T-cells may be activated by interleukin-2, interleukin-4 and other interleukins.

Preferably, the recognition agent is a monoclonal antibody or fragment thereof directed against an epitope of a leukocyte-associated antigen which is only expressed after activation, or which exhibits enhanced cell surface expression following activation. A useful activation marker within the present invention is one associated with a leukocyte surface antigen involved in chemotaxis, phagocytosis or cell killing which are functions normally enhanced with respect to activated leukocytes.

Exemplary epitopes useful as activation markers include epitopes associated with the lymphocyte function associated antigens (LFA-1, LFA-2 and LFA-3), LEU-CAM, CD2, the LFA ligand, complement receptors CR1 and CR3, Fc receptors (I, II, III), a leukotriene receptor or a chemotactic factor receptor. Preferable chemotactic factor receptors recognize and bind C5a, C3a and formyl-methionine-leucine-phenylalanine (fMLP). Complement receptors include those for C1q and C3 fragments.

Recognition agents useful in the present invention selectively interact with activated leukocytes. That is, recognition agents of the present invention exhibit at least a 10-fold preference for binding to activated leukocytes over binding to non-activated leukocytes. For example, leukocyte receptor inhibitors are useful as recognition agents within the present invention.

The relationship between these antigens/epitopes and useful recognition agents may be further elucidated by way of example. As mentioned above, the C3 receptor is up-regulated upon leukocyte activation. As a result, monoclonal antibodies or fragments thereof specific for CR3 may be used as recognition agents. Normally, the expression of such receptor is below $10^3$ sites/cell and, therefore, insufficient for imaging. Up-regulation upon activation would both increase receptor number (making the receptor suitable for imaging) and increase receptor affinity (making it appropriate for imaging with labeled ligand). Thus, a ligand like a complement fragment may be labeled and used as a recognition agent in the practice of the present invention. Other exemplary ligands for up-regulated receptors include chemotactic peptides like fMLP, peptides derived from C3a and C5a capable of binding their respective receptors, immunoglobulin Fc peptides capable of binding Fc receptors, and complement components like C1q or C3 fragments capable of binding their respective receptors.

An embodiment of the present invention features a monoclonal antibody or fragment thereof as a recognition agent directed against complement fragments that are bound at inflamed tissue sites or adsorbed to activated leukocyte receptors. A preferred embodiment of the present invention involves the use of a monoclonal antibody directed against C3dg. C3dg is an especially useful target for several reasons. First, C3dg is a cell- or tissue-bound activation product of the complement cascade, and will be present as a result of complement activation through the classical or alternative pathways. Second, since C3dg is the final degradation product of C3, antibodies directed to C3dg will assuredly react with tissue sites of activation, as opposed to antibodies directed to C3, C3b, or iC3b, which may react to determinants lost with further degradation. Third, antibodies to C3dg will be more sensitive in detecting inflammation than antibodies to other complement components, since C3 activation represents the point of amplification in the complement cascade. For instance, for each molecule of C1q bound to cells or tissues, 100 molecules of C3b are bound. Fourth, antibodies to C3dg would have high selectivity for sites of inflammation similar to other antibodies to C3 fragments, since the presence of C3dg at any tissue site would require three different proteolytic cleavage steps, each regulated by a variety of mechanisms.

A further embodiment of the present invention involves the use of a monoclonal antibody or fragment thereof directed against activated leukocytes that does not exhibit substantial interaction with non-activated leukocytes. Use of this type of monoclonal antibody permits a qualitative (rather than merely quantitative) distinction to be made between activated and non-activated leukocytes by the label-recognition agent conjugate.

A preferred embodiment of the present invention involves the use of a conformation-dependent determinant on a cell surface lymphoid activation marker. The specificity of such conformation-dependent determinant is associated with leukocyte adhesion or aggregation that may occur when an activated leukocyte contacts vascular endothelium, undergoes phagocytosis of a microorganism or adheres to a target cell, as in a cytolytic process. For example, vascular endothelium expresses an adhesion protein designated I-CAM. I-CAM interacts with PMN surface LFA antigens to cause adherence of PMNs to the vascular endothelium. When an activated PMN undergoes adhesion to vascular endothelium, conformational changes occur in leukocyte membrane proteins that contact the vascular endothelium. Since these unique conformation-dependent epitopes are exposed only upon adhesion of PMNs to the vascular endothelium, an antibody directed at said epitopes will only recognize PMNs at sites of inflammation. This LFA/I-CAM adherence is markedly increased by prior activation of PMNs which up-regulates LFA expression.

Similar determinants are exposed upon homotypic aggregation of activated leukocytic cells. Moreover, PMNs express a marker that is substantially equivalent to I-CAM. This determinant is designated LEU-CAM and is capable of interacting with LFA in furtherance of homotypic aggregation of PMNs. Such homotypic aggregation, thus appears to be LFA and LEU-CAM mediated. As a result, a monoclonal antibody directed accessible to conformation-dependent epitopes expressed by homotypic aggregates of leukocytes but not non-aggregated leukocytes will exhibit specificity for activated leukocytes.

Monoclonal antibodies or fragments thereof of the present invention may be prepared according to conventional techniques. See, for example, Kohler and Milstein (1975, Nature 256: 495–97; 1976, Eur. J. Immunol. 6: 511–519). Antibodies to conformation-dependent determinants or activation markers are generated, for example, by immunizing mice with homotypic aggregates of activated PMNs, monocytes, cultured myelomonocytic cell lines (such as U-937 or THP-1), or with other suitable cell sources bearing leukocyte markers like LFA. In a preferred embodiment, mice are immunized with PMNs that are pooled from normal donors and activated with GM-CSF in the presence of human serum until aggregation occurs. Activation of PMNs allows for up-regulation of LFA, complement and chemotactic peptide receptors, as well as the adsorption of complement components to activated cells. Hybridomas generated by the immunogen are then screened against the original immunizing cells adsorbed to poly-L-lysine-coated microtiter plates or against non-activated pooled PMNs in the presence of human serum. Desired antibodies will recognize activation markers as well as conformation dependent determinants. The monoclonal antibodies can then be further screened against inflammatory lesions by using immunoperoxidase techniques.

Eosinophilotactic peptides may also be used as recognition agents within the present invention. Exemplary peptides are VGDE (val-gly-asp-glu), VGSE (val-gly-ser-glu), VGAE (val-gly-ala-glu) and AGSE (ala-gly-ser-glu). These exemplary peptides are described in PNAS, 72: 4123 (1975), Immunology, 32: 57 (1977) and Clinical Experimental Immunology, 43: 399 (1981). Eosinophilotactic peptides may be labeled through conventional techniques, preferably through the attachment of a spacer portion having a terminal tyrosine residue (the tyrosine residue may, of course, be attached after the spacer portion has been bound to the peptide). The tyrosine residue may then be radiolabeled.

As another recognition agent of the present invention, there is contemplated a chemotactic factor. A chemotactic factor is a factor that attracts polymorphonuclear leukocytes through a process called chemotaxis. Exemplary chemotactic factors useful in the present invention include chemotactic peptides such as fMLP and pop, ides of complement proteins, fragments thereof or derivatives or analogs thereof. Longer chemotactic peptides, such as fibrinopeptide B (pyroglu-G-V-N-D-N-E-E-G-F-F-S-A-R), may also be used in accordance with the present invention. Preferred complement proteins useful as recognition agents are C3a and C5a, fragments thereof or derivatives or analogs thereof. Exemplary analogs are:

f-norLeu-L-P-norLeu-Y-K, wherein the tyrosine (Y) residue may be radiolabeled directly; and
f-norLeu-L-P-norLeu-;
boc-L-P-L-P-;
boc-M-L-P-;
boc-P-L-F-L-F-;
boc-P-$L_b$-P-$L_b$-F-; and
f-M-L-Y-, wherein boc is T-butoxycarbonyl, $L_b$ is D-Leu and wherein the analogs may be labeled through conventional techniques, preferably through the attachment of a spacer portion having a terminal tyrosine residue (the tyrosine residue may, of course, be attached after the spacer portion has been bound to the peptide). The tyrosine residue may then be radiolabeled. These exemplary peptide analogs are described in Science, 205: 1412 (1979), Biochim. Biophys. Acta, 602: 285 (1980), Nature, 272: 462 (1978), PNAS, 73: 2439 (1976) and Biochem. Biophys. Res. Comm., 30: 464 (1978).

Also useful as recognition agents in the practice of the present invention are chemotactic peptide receptor inhibitors. Such inhibitors will bind to the chemotactic peptide receptor with high affinity. Peptides of complement protein C3a des Arg are also useful as recognition agents.

Chemotactic peptides may be prepared synthetically by conventional techniques. One embodiment of the label-recognition agent conjugate of the present invention involves the incorporation of D-amino acid(s) into a synthetic peptide chain, thereby decreasing in vivo degradation of the synthetic peptide. Degradative processes of the host recognize naturally-occurring L-amino acids. Thus, incorporation of one or more D-amino acids into the synthetic peptide enhances the stability of the peptide in vivo.

Another embodiment of the imaging method of the present invention as related to small synthetic peptides used as recognition agents involves the additional steps of:

(4) comparing inflammation site localization of the chemotactic peptide and reticuloendothelial system localization of the peptide, wherein exhibition of a substantial affinity of the peptide for circulating or reticuloendothelial cells necessitates step (5); and, if necessary, (5) altering the amino acid sequence of the peptide through addition or deletion of amino acids, to more closely correlate the peptide structure with that bound by high affinity receptors of the activated leukocytes and less closely correlate with that bound by receptors of non-activated cells, thereby producing a modified peptide capable of preferentially binding to activated leukocytes at sites of inflammation.

Labeled peptide can be compared for binding to activated and non-activated cells. Modified or non-modified peptides are screened against activated and non-activated PMN or monocytes for binding. A comparison of the difference in selectivity of peptides bound to activated and non-activated cells at different concentrations will indicate relative specificity of the peptide for activated and non-activated cells.

The comparison of step (4) may also be accomplished through analysis of an image obtained as described in steps (1)–(3). Such analysis is within the ordinary skill of a diagnostician familiar with diagnostic imaging of this type.

The alteration of step (5) may be accomplished by conventional protein synthetic techniques, following analysis of the binding to activated and non-activated cells. Activated leukocytes express receptors of higher affinity than non-activated leukocytes. Thus, recognition agents may be modified to more specifically associate with these high affinity receptors. Such alteration of recognition agents may be steric or chemical. That is, the change can serve to improve the steric "fit", i.e., the actual three-dimensional structural congruence of the peptide and the target leukocytes, or to improve the chemical "fit", i.e., the correspondence of positively and negatively charged amino acids between the peptide and the target leukocyte receptor.

Enhanced target cell label retention, may be obtained by substituting longer, more hydrophobic or charged amino acids to the chemotactic protein. These modified peptides may enhance the accumulation of label at target tissue sites by increasing the peptide's ability to anchor to target cells, for example, by incorporation of a "spacer" amino acid portion to increase the length of the targeting peptide thereby increasing the accessibility of the peptide binding site to appropriate receptors on target cells.

Additional hydrophobic or like-charged polar "spacer" amino acid sequences can also be used to enhance peptide access to a receptor. For example, a chain of glycines (poly-G) could be added to the carboxy terminus of fMLP to increase chain length. A plurality of alanines (poly-A) may be added to produce a longer, more hydrophobic moiety. Aspartic acid (D) residues can be added to obtain a longer, negatively charged recognition agent while arginine (R) residues will impart positive charge as -well as increased length. In each case, it may be necessary to include another amino acid, such as cysteine, to permit binding of the modified chemotactic peptide to a chelating compound.

Another procedure that may alter the serum half-life of the peptide (e.g., deliver an increased percentage of dose/gram to site of inflammation) and increase affinity of the peptide for the target is conjugation of the peptide or peptide-spacer to a macromolecular carrier, such as albumin.

Radiolabeling of antibodies and proteins may be accomplished through known techniques, such as those described in European Patent Application Publication Nos. 0188256, 0289187 and 0203764. Alternatively, smaller, synthetically prepared peptides, such as fMLP, may be labeled by other techniques. For example, a synthetic peptide may be radiolabeled via tyrosine, lysine or cysteine or phenylalanine residue or analog thereof added to the peptide during conventional protein synthesis. Labeling such synthetic peptides may be done, for example, in two steps. First, the peptide having an additional residue is synthesized. Second, the residue is labeled by known techniques such as linking via a hetero bi-functional chelate.

Within the present invention, the labeled recognition agent is infused into a patient whose tissue sites are to be imaged. This infusion may be conducted in any manner adequate to deliver the labeled recognition agent to the bloodstream of the patient. Exemplary of acceptable administration routes are intraperitoneal, subcutaneous, intradermal, intraarterial or intravenous injection. The mode of administration is typically chosen according to the projected ultimate destination of the labeled recognition agent. Such infusions may be given as single or multiple injections. The labeled recognition agent may be administered through injection directly into the damaged tissue location, where convenient.

In vivo administration of labeled recognition agent may involve the use of pharmaceutical compositions in which the labeled recognition agent is dispersed in a pharmaceutically acceptable carrier. Exemplary of such pharmaceutically acceptable carrier is physiological saline or a physiologically acceptable buffer solution.

Generally, the amount of the labeled recognition agent administered to a patient will depend primarily on the size of the patient and the purpose of the administration. However, the patient's physiological condition and the tissue site to be imaged or treated, if known, may affect the amount of labeled recognition agent necessary to obtain a usable image. Dosage of labeled recognition agent may readily be determined by one of ordinary skill in diagnostic imaging. A typical dose of radiolabeled recognition agent is between about 1 and about 3000 mCi. In humans, a standard imaging dose will be from about 1 to about 50 mCi, with about 10 to about 30 mCi being typical.

The imaging of the present invention may be accomplished with the aid of one of the many commercially available imaging cameras, such as the Picker Digital Dynascan camera, the Raytheon LFOV Anger gamma camera and the gamma camera STARCAM made by General Electric corporation. Visualization of sites of inflammation may be obtained by planar or single photon emission computed tomographic (SPECT) scans.

The time lapse between infusion of the labeled recognition agent and scan or imaging will vary somewhat with the patient's characteristics, i.e., body weight and condition, as well as the administration route, recognition agent and label used. Typically, a lapse of between 3 and 144 hours is required to allow the labeled recognition agent the opportunity to migrate to the target tissue and clear from uninvolved tissue. An appropriate time lapse is readily determinable by a person ordinarily skilled in diagnostic imaging.

Images produced according to the present invention may aid in the detection of tissue damage mediated by inflammation. A diagnostician will recognize image patterns characterizing such an ailment. Also, the images produced according to the present invention will provide the diagnostician with information regarding the extent of tissue damage or area susceptible to tissue damage, as with myocardial infarction. Also, a sequence of images of an afflicted tissue site will permit monitoring of treatment protocols designed to alleviate inflammation.

Another aspect of the present invention involves a method of imaging a tissue site of inflammation including:

(1) infusing non-labeled recognition agent into a patient, wherein the agent is capable of interacting with activated leukocytes accumulated at the tissue site;

(2) labeling a recognition agent;

(3) infusing labeled recognition agent into the patient; and (4) imaging said tissue site, whereby medical conditions involving tissue inflammation may be detected, evaluated and monitored. As can be readily appreciated, the exact ordering of steps, most notably steps (1) and (2) may be altered without materially altering the procedure.

This embodiment of the present invention addresses the problem of accumulation of labeled recognition agent within the reticuloendothelial system or on circulating cells. Accumulation in the RES will decrease the clarity of the image by creating "visual background".

That is, if normal tissue expression of the antigen or determinant recognized by the labeled antibody is more accessible to recognition agent than the inflamed tissue site of the antigen or determinant, normal tissue sites may be saturated before the inflamed tissue sites are filled. See, for example, co-pending U.S. patent application, Ser. No. 917,176 filed on Oct. 9, 1986, entitled "METHODS FOR IMPROVED TARGETING OF ANTIBODY FRAGMENTS AND CONJUGATES THEREOF," now abandoned in favor of U.S. continuation-in-part application Ser. No. 107,136, filed on Oct. 9, 1987, entitled "METHODS FOR IMPROVED TARGETING OF ANTIBODY, ANTIBODY FRAGMENTS, HORMONES AND OTHER TARGETING AGENTS, AND CONJUGATES THEREOF," allowed Jan. 29, 1991.

For example, antigen-bearing normal cells within the bloodstream will be more accessible to "cold" antibody than non-circulating inflammatory tissue cells. Thus, "cold" agent will associate preferentially with the more accessible, peripheral, antigen-bearing normal cells. As a result, subsequently infused labeled or "hot" antibody will be more likely to reach and bind the less accessible, antigen-bearing inflammatory tissue cells. If a significant, accessible normal tissue antigen pool does not exist, no pre-infusion of "cold" agent is necessary.

For "cold" infusion, a non-labeled recognition agent is infused into a patient whose tissue sites are to be treated in the same or different manner than with the labeled recognition agent. In vivo administration of non-labeled recognition agent may involve the use of pharmaceutical compositions in which dispersion in a pharmaceutically acceptable carrier is necessary or desirable. Exemplary of such a pharmaceutically acceptable carrier is physiological saline or a physiologically acceptable buffer solution.

Generally, the amount of non-labeled recognition agent administered to a patient will depend primarily on the size of the patient. However, the patient's physiological condition and the tissue site to be imaged, if known, may affect the amount of non-labeled recognition agent required to obtain a diagnostic image substantially free of background. Dosage of non-labeled recognition agent may readily be determined by one of ordinary skill in diagnostic imaging. Saturation of peripheral cell sites may be monitored by removing samples of circulating cells and measuring percent saturation by flow cytometry.

The time lapse between infusion of non-labeled recognition agent and labeled recognition agent will vary somewhat with the patient's characteristics (i.e., body weight and condition), as well as with the administration route, recognition agent and label used. The time lapse necessary to allow the non-labeled recognition agent adequate opportunity to associate with normal cells is readily determinable by a person ordinarily skilled in diagnostic imaging.

In this aspect of the present invention, the "hot" recognition agent need not exhibit marked specificity for activated over non-activated leukocytes since the "cold" recognition agent will bind sites located on the more easily accessible peripheral leukocytes. However, further enhancement of label at target tissue sites can be attained if the "hot" recognition agent binds preferentially to activated leukocytes.

When synthetic peptides are used as recognition agents, a second level of reduction in visual background is possible regarding images produced by the invention. The method may be performed as above with the further steps of:

(5) comparing inflammation site localization of the chemotactic peptide and reticuloendothelial system localization of the peptide, wherein exhibition of a substantial affinity of the peptide for circulating or reticuloendothelial cells necessitates step (6); and, if necessary, (6) altering the amino acid sequence of the peptide through addition or deletion of amino acids, so as to more closely correlate the peptide structure with that bound by high affinity receptors of the activated leukocytes and less closely correlate with that bound by receptors of non-activated cells, thereby producing a modified peptide capable of preferentially binding to activated leukocytes at sites of inflammation.

The first and second aspects of the present invention described above involves the in vivo association of the labeled recognition agent with target leukocyte cells. The third aspect of the present invention involves ex vivo association of recognition agent with leukocyte cells. In vivo association techniques may also be used in conjunction with the ex vivo association within the second aspect of the present invention.

Specifically, the third aspect of the present invention contemplates a method of imaging a tissue site of inflammation involving:

(1) labeling a recognition agent, wherein the agent is capable of interacting with a leukocyte binding moiety;

(2) withdrawing leukocytes from a patient;

(3) incubating leukocytes of step (2) with labeled recognition agent of step (1);

(4) infusing into the patient labeled recognition agent and leukocytes incubated in step (3); and (5) imaging the tissue site, whereby medical conditions involving tissue inflammation may be detected, evaluated and monitored. As can be readily appreciated, the exact ordering of steps, most notably steps (1) and (2) may be altered without materially altering the procedure.

The method of this aspect of the present invention may further include an activation step following withdrawal step (2). That is, the withdrawn leukocytes can optionally be activated by incubation with an activation agent as previously described or by other means suitable to accomplish such activation.

Exemplary leukocyte binding moieties of the present invention are chemotactic peptide receptors. These receptors and recognition agents useful in targeting such receptors have been previously discussed.

Complement receptors are also useful leukocyte binding moieties within the third aspect of the present invention. C3a and C5a receptors are especially useful in the practice of the present invention. The corresponding complement components or analogs or derivatives thereof may be used as recognition agents within these embodiments of the present invention.

An additional leukocyte binding moiety is a leukocyte surface antigen which up-regulates upon leukocyte activation. In this embodiment, Fab or F(ab')$_2$ fragments of monoclonal antibodies capable of recognizing an up-regulated leukocyte surface antigen can be used as recognition agents.

Another exemplary leukocyte binding moiety of the present invention is an adhesion protein. Adhesion proteins are those which are involved in the adhesion of leukocytes to each other or other cells. Exemplary adhesion proteins are LFA-1, LFA-2 and LFA-3.

Additionally, adhesion protein receptors are useful as leukocyte binding moieties in the practice of this aspect of the present invention. Exemplary adhesion protein receptors are located, for example, on the vascular endothelium (I-CAM) or on the leukocytes themselves (LEU-CAM).

This aspect of the present invention may be described in the following manner. Labeled recognition agent directed to a receptor for adhesion proteins is incubated together with activated or non-activated, autologous PMNs or monocytes followed by reinfusion into the host.

Labeled leukocytes will accumulate at sites of inflammation. This represents an improvement over prior art processes which involved either oxidative cell surface labeling or incubation of leukocytes with whole antibody specific to non-activation markers.

When non-activated leukocytes are used in incubation step (3), accumulation of label at target tissue sites will be enhanced due to migration of reinfused autologous leukocytes associated with recognition agent-label conjugates to the target tissue site as well as by virtue of the specificity of the recognition agent for activated leukocytes located at the target site.

In the use of activated leukocytes in incubation step (3), label localization improves due to an increase in activation markers. However, coincident with this up-regulation, LFA expression is enhanced. Enhanced LFA expression leads to increased interaction with I-CAM sequences on vascular endothelium and reduced extravasation of activated PMNs into tissue. Enhanced LFA expression also results in increased aggregation with LEU-CAM sequences on other activated leukocytes and homotypic aggregation of those activated leukocytes.

In addition to antibody to LFA, peptides containing RGDS (arginine-glycine-aspartic acid-serine) sequences or other "I-CAM like" sequences, can be used as the labeled recognition agent. By "I-CAM like" sequences, there are contemplated sequences which are substantially functionally equivalent to I-CAM. For the purposes of this invention, LEU-CAM is a substantially functional equivalent of I-CAM.

Thus, in an example of this aspect of the present invention, PMNs are activated by GM-CSF or one or more other activation agents, and then incubated with labeled Fab or F(ab')$_2$ fragments of an antibody to LFA capable of inhibiting interaction with I-CAM, such as the antibodies 4F-2 and OKM-1. Since receptors for chemotactic stimuli are unblocked, cells can still chemotax efficiently and extravasate. As anti-LFA antibody fragment is lost from the cell surface of PMNs, cells which have extravasated into sites of inflammation will be blocked from re-egress into the circulation.

In a modification of this aspect, Fab or F(ab')$_2$ to LFA can be infused upon reinjection of labeled, activated autologous PMNs, to maintain the blockade of LFA interaction with I-CAM and to ensure that cells do not accumulate in the RES.

An application of the present invention involves diagnostic kits useful for in vivo imaging of tissue sites of inflammation comprising:

(1) recognition agent;

(2) instructions for labeling and administering the agent in a manner and amount sufficient to permit a diagnostic image to be obtained from tissue of the patient.

As a diagnostic kit, there is contemplated a collection of materials within a box or other container that are capable of being used in the present invention with little additional processing by the end user. Such an end user need only provide items which are typically available to the practicing end user, such as imaging equipment, radiolabel and possibly some portion of the equipment necessary for administration of the agent to the patient. For example, sterile vials capable of use with standard syringes could be employed as containers for lyophilized recognition agent or solutions containing the recognition agent dispersed in a physiologically acceptable liquid. When lyophilized recognition agent is used, a sterile vial containing a physiologically acceptable buffer solution may be included in the diagnostic kit. The instructions for use of the diagnostic kit may be affixed to the container or be included as a separate insert within the container or both.

An embodiment of this aspect of the present invention involves a diagnostic kit, as previously described, which also contains an additional amount of recognition agent for ultimate use as non-labeled recognition agent. That is, a second sterile vial containing lyophilized recognition agent or a solution of recognition agent in a physiologically acceptable liquid is provided. When lyophilized recognition agent is used, an additional amount of physiologically acceptable buffer may be included in the kit.

Also, the present invention contemplates diagnostic kits useful for in vivo imaging of an ischemic tissue site in a patient suffering from a condition characterized by transient decrease in blood flow to issue sites comprising:

(1) recognition agent;

(2) instructions for labeling and administering the agent in a manner and amount sufficient to permit a diagnostic image to be obtained from ischemic tissue of the patient.

An embodiment of this aspect of the present invention involves a diagnostic kit, as previously described, which also contains an additional amount of recognition agent for ultimate use as non-labeled recognition agent.

A decrease in blood flow to a tissue site causes a temporary deficiency of oxygen in that tissue. An inadequate oxygen supply results in tissue damage to deprived tissue sites. Cell death and release of mitochondrial proteins capable of binding C1q (the first component of the complement cascade) occur due to inadequate oxygen supply. Subsequent activation of the complement cascade and initiation of cellular infiltration (primarily by PMNs) result in further damage to cells.

For example, one of the earliest manifestations of myocardial infarction is ischemia associated with a reduction in blood flow to the heart muscle due to occluding clot formation. Ischemia, even if only transient, results in death of some cells and release of mitochondrial proteins capable of binding to C1q. This event leads to activation of the complement cascade and cellular infiltration which, in turn, result in additional cellular damage and infarct formation. Thus, ischemic heart muscle may be imaged in accordance with the present invention prior to the onset of myocardial infarction with its attendant inflammation. Ischemic heart muscle, hypoxic bowel tissue, vascular collagen diseased tissue, and tissue sites afflicted with cancer and characterized by decreased blood flow are exemplary of ischemic tissue sites.

Another application of the present invention involves a method of detecting a tissue site of inflammation in a patient comprising:

(1) labeling a recognition agent, wherein the agent is capable of interacting with activated leukocytes accumulated at the tissue site;

(2) infusing labeled recognition agent into the patient;

(3) imaging the tissue site; and (4) analyzing the image obtained in step (3) for an accumulation of labeled recognition agent characteristic of tissue inflammation. The detection method may also be accomplished in conjunction with the autologous leukocyte activation embodiment of the present invention.

This application features analyzing step (4). Such analysis may be accomplished visually by an experienced diagnostician. That is, diagnosticians familiar with images of inflamed tissue would be able to ascertain that inflammation is or is not present at an imaged tissue site by recognizing patterns characteristic of inflammation in the image obtained from a given patient. Analyzing step (4) may also be accomplished "mechanically" by a computer having a library of previously analyzed images stored in its memory. A match or close correspondence of the test image with a stored image would indicate the presence or absence of inflammation.

A further application of the present invention contemplates a method of monitoring the efficacy of treatment of tissue inflammation in a patient by:

(A) preparing a sequence of diagnostic images of an afflicted tissue site during the treatment, each image being prepared by a process comprising:

(1) labeling a recognition agent, wherein the agent is capable of interacting with activated leukocytes accumulated at the tissue site;

(2) infusing labeled recognition agent into the patient; and (3) imaging the tissue site; and (B) analyzing the sequence of images obtained in step (A) to determine response of the patient to the treatment. Again, this monitoring method may be accomplished in conjunction with the autologous leukocyte activation embodiment of the present invention as well.

This aspect of the present invention features serial imaging, i.e., a sequence of diagnostic images of a tissue site prepared over time and accumulated in a storage area, to monitor the efficacy of a treatment protocol. Time lag between images will principally be dictated by the condition being treated and be limited by the time required for the imaging process itself.

Analysis step (B) may be accomplished visually by any experienced diagnostician. That is, diagnosticians familiar with images of inflamed tissue would be able to ascertain that inflammation has increased, decreased or remained approximately the same over time by comparing images of the inflamed tissue taken at various time intervals. In other words, serial images would be compared to determine if the treatment protocol being administered to the patient is successful. A decrease in inflammation, ascertainable from serial images of a single tissue site, would indicate a successful treatment strategy. In fact, a person having less familiarity with inflamed tissue and/or images thereof would be able to make a rough determination of the efficacy of the treatment through a comparison of serial images.

An efficacy analysis may also be accomplished "mechanically" by a computer having the serial images stored in its memory. A data point by data point comparison may then be carried out by the computer to determine whether the inflamed tissue has been successfully treated.

To summarize the examples that follow, Examples I II, III and IV describe the preparation of labeled chemotactic peptide and derivatives thereof; Example V describes peptide-label conjugation; Examples VI and VII describe methods of imaging tissue sites using labeled chemotactic peptides as recognition agents; Examples VIII and IX describe the preparation of monoclonal antibodies; Examples X and XI describe the preparation of labeled monoclonal antibodies; Examples XII and XIII, XIV and XV describe methods of imaging tissue sites using labeled monoclonal antibodies as recognition agents; Examples XVI and XVII describe diagnostic kits; Examples XVIII and XIX describe methods of monitoring treatment of tissue damage; Example XX describes activation of PMNs; Example XXI describes activation of monocytes; and Example XXII describes a method of imaging involving infusion of autologous leukocytes. These examples are offered as illustrations of the present invention and not as limitations thereof.

EXAMPLE I

Preparation of Labeled Chemotactic Peptide

The chemotactic peptide met-leu-phe having an additional cysteine residue is synthesized using tea-bag methodology and solid phase peptide synthesis procedures described by Merrifield et al. (*Biochemistry* 21: 5020–31, 1982) and Houghten (*Proc. Natl. Acad. Sci. (USA)* 82: 5131–35, 1985) or using a commercially available automated synthesizer, such as the Applied Biosystems 430 A or using other standard biochemistry techniques. The peptide is cleaved from the resin using HF and established procedures and extracted with dilute acetic acid. The peptide is lyophilized and is purified using reverse phase HPLC on a Vydac C-4 analytical column (The Separations Group, Hesperia, Calif.) and a linear gradient of 0.5–1.0%/min from 100% water+0.1% v/v trifluoroacetic acid to 100% acetonitrile+0.1% trifluoroacetic acid. The peptide is N-formylated via reaction with acetic anhydride in 98% formic acid for 1 hour at 25° C. as described in *J. Am. Chem. Soc.*, 80: 1154 (1958).

A solution of Tc-99m-tartrate is prepared by adding 1.1 ml of degassed distilled water containing 9% ethanol to 100 micrograms (ca. 0.43 micromoles) $SnCl_2$, 75 mg (ca. 0.32 mmol) disodiumtartrate, and 3.2 mCi sodium (Tc-99m) pertechnetate. This mixture is heated at 50° C. with a water bath for 15 minutes. After cooling in a separate container, 100 microliters of the Tc-99m-tartrate solution, 200 microliters of 0.2M pH 8.0 sodium phosphate buffer, and 100 micrograms of prepared chemotactic peptide are admixed. The total volume of the solution is adjusted to 0.5 ml with an aqueous solution of 0.15M sodium chloride and is incubated at 50° C. for 60 minutes.

EXAMPLE II

Preparation of Stabilized, Labeled Chemotactic Peptide

The chemotactic peptide met-leu-phe having an additional Gly-Gly-Lys moiety is synthesized using teabag methodology and solid phase peptide synthesis procedures described by Merrifield et al. (*Biochemistry* 21: 5020–31, 1982) and Houghten (*Proc. Natl.. Acad. Sci. (USA)* 82: 5131–35, 1985) or using a commercially available automated synthesizer, such as the Applied Biosystems 430 A or using other standard biochemistry techniques. The peptide is cleaved from the resin using HF and established procedures and extracted with dilute acetic acid. The peptide is lyophilized and is purified using reverse phase HPLC on a Vydac C-4 analytical column (The Separations Group, Hesperia, Calif.), and a linear gradient of 0.5–1.0%/min from 100% water+0.1% v/v trifluoroacetic acid to 100% acetonitrile+0.1% trifluoroacetic acid. The peptide is N-formylated via reaction with acetic anhydride in 98% formic acid for 1 hour at 25° C. as described in *J. Am. Chem. Soc.*, 80: 1154 (1958). Iodine labeling of the lysine residue is accomplished as described by Panuska and Parker (*Analytical Biochemistry* 160: 192–201, 1987).

EXAMPLE III

Preparation of Chemotactic Peptide Derivatives

The chemotactic peptide analog boc-L-F-L-F having a chain of amino acids, such as -G-G-G-G-G-Y, at its amino terminus is synthesized as described in *Biochim. Biophys. Acta* 602: 285 (1980) or using a commercially available automated synthesizer, such as the Applied Biosystems 430 A or using other standard biochemistry techniques. The peptide is lyophilized and is purified using reverse phase HPLC on a Vydac C-4 analytical column (The Separations Group, Hesperia, Calif.), and a linear gradient of 0.5–1.0%/minute from 100% water+0.1% v/v trifluoroacetic acid to 100% acetonitrile+0.1% trifluoroacetic acid. Iodine labeling of the peptide is accomplished as described in European Patent Application publication No. 0289187. The longer chemotactic peptide derivative enhances target cell label retention.

EXAMPLE IV

Preparation of Chemotactic Peptide Derivatives

The chemotactic peptide analog f-norLeu-L-F-nor-Leu-Y-K is synthesized as described in *Science*, 205: 1412 (1979) or using a commercially available automated synthesizer, such as the Applied Biosystems 430 A or using other standard biochemistry techniques. The peptide is lyophilized and is purified using reverse phase HPLC on a Vydac C-4 analytical column (The Separations Group, Hesperia, Calif.), and a linear gradient of 0.5–1.0%/minute from 100% water+0.1% v/v trifluoroacetic acid to 100% acetonitrile+0.1% trifluoroacetic acid. Radiolabeling of the peptide is accomplished as described in European Patent Application publication no. 0203764. This charged chemotactic peptide derivative enhances target cell label retention.

EXAMPLE V

Peptide-Label Conjugations

A Tc-99m chelate is conjugated to the unlabeled chemotactic peptide of Examples I, II, III or IV as follows. 75 mCi of Tc-99m chelated by N, N'-bismercaptoacetyl 4,5-diaminopentanoic acid is prepared by dithionite reduction of Tc-99m pertechnetate at basic pH with 25 micrograms of the $N_2S_2$ ligand. The acid is activated by adding the above complex at pH 7 in 0.5 ml water to 100 microliters of water:acetonitrile (1:9) containing 3.0 milligrams of 2,3,5,6-tetrafluorophenol and 100 microliters of water:acetonitrile (1:9) containing 7.5 milligrams of 1-cyclohexyl-3-(2-morpholinoethyl)carbodiimide (morpho CDI). After storing for 18 hours at room temperature, the mixture is purified using a Baker-10 SPE reversed phase $C_{18}$ column. The column is conditioned with 2 milliliters of ethanol and is then washed with HPLC grade water. The reaction mixture is then added to the column, the column is then washed four times with 2 milliliter volumes of 10% methanol in 0.01 sodium phosphate, pH 7.0 and the ester complex is finally eluted with 2.5 milliliter portions of acetonitrile.

To a 2 milliliter vial is added 4.5 mCi of activated ester complex in acetonitrile, the solvent is evaporated in a nitrogen stream, and 0.4 milliliters of sodium borate (0.5M, pH 9.0) is added. While agitating, the chemotactic peptide is added and incubation at room temperature is conducted for 30 minutes.

EXAMPLE VI

Method of Imaging—Chemotactic Peptide as Recognition Agent 50 mCi of the labeled chemotactic peptide of EXAMPLE II is admixed with a pharmaceutically acceptable saline solution. This mixture is administered subcutaneously to the patient. After 24 hours, a diagnostic image is prepared through the use of a Raytheon LFOV Anger gamma camera.

EXAMPLE VII

Method of Imaging—Chemotactic Peptide as Recognition Agent 30 mCi of the labeled chemotactic peptide of EXAMPLE III is admixed with a pharmaceutically acceptable saline solution. This mixture is administered intravenously to the patient. After 18 hours, a diagnostic image is prepared through the use of a STARCAM gamma camera made by General Electric Corporation.

EXAMPLE VIII

Monoclonal Antibody Preparation

Mice are immunized with homotypic aggregates of activated PMNs pooled from normal donors. This pooling of PMNs is accomplished through the withdrawal of blood (in amounts of approximately 150 cc) by venipuncture in heparinized tubes and mixing with an equal volume of 3% dextran in phosphate-buffered saline (PBS). After sedimentation at $1 \times g$ for 10 minutes at room temperature, the leukocyte-rich plasma is layered on top of lymphocyte separation medium (LSM, Organon Technica, Durham, N.C.). PMNs are purified by treating the PMNs and the red blood cell (RBC) pellet with RBC lysing solution (0.800% w/v $NH_4Cl$, 0.1% w/v $KHCO_3$, 37.0 mg tetrasodium EDTA in 100 ml water at pH 7.3). After incubating approximately 5 minutes at room temperature, the volume is increased three times with PBS and the cells are washed twice by centrifugation. The PMNs are incubated for 15 to 30 minutes with 100 U/ml GM-CSF in the presence of human serum to generate activated PMNs which are capable of forming homotypic aggregates.

These aggregated PMNs are then injected into mice as an immunogen. Hybridomas generated by the immunogen are then screened against activated or non-activated pooled PMNs in the presence of human serum. Desirable antibodies are those that recognize activation markers as well as conformation-dependent determinants (in this case, PMN-PMN aggregates). The antibodies identified as desirable are further screened against inflammatory lesions using immunoperoxidase techniques.

EXAMPLE IX

Monoclonal Antibody Preparation

Mice are immunized with heterotypic aggregates prepared in vitro and having activated PMNs pooled from normal donors as one component of the heterotypic aggregate. This pooling of PMNs is accomplished through the withdrawn of blood (in amounts of approximately 150 cc) by venipuncture in heparinized tubes and mixing with m equal volume of 3% dextran in phosphate-buffered saline (PBS). After sedimentation at 1×g for 10 minutes at room temperature, the leukocyte-rich plasma is layered on top of lymphocyte separation medium (LSM, Organon Technica, Durham, N.C.). PMNs are purified by treating the PMNs the and red blood cell (RBC) pellet with RBC lysing solution (0.800% w/v $NH_4Cl$, 0.1% w/v $KHCO_3$, 37.0 mg tetrasodium EDTA in 100 ml water at pH 7.3). After incubating approximately 5 minutes at room temperature, the volume is increased three times with PBS and the cells are washed twice by centrifugation.

The activated PMNs are incubated with either vascular endothelial cells or portions thereof, bacteria or other pathogenic organisms or target tissue (tissue afflicted with inflammation). This incubation is conducted for a time sufficient (approximately 30 minutes) to permit association of the activated PMNs with the vascular endothelial cells, the commencement of phagocytosis with respect to the pathogenic organisms, or attachment of the activated PMNs and the target cells.

One type of heterotypic aggregate is then injected into mice as an immunogen. Hybridomas generated by the immunogen are then screened against activated or non-activated pooled PMNs in the presence of human serum. Desirable antibodies are those that recognize activation markers as well as conformation-dependent determinants (in this case, epitopes present on PMN-vascular endothelium aggregates, PMNs undergoing phagocytosis or PMN-target cell aggregates). The antibodies identified as desirable are further screened against inflammatory lesions using immunoperoxidase techniques.

EXAMPLE X

Antibody-Label Conjugation

In an evacuated vial is combined 100 microliters of water, 100 microliters acetonitrile, 100 microliters of citrate solution (28.8 milligrams, $1.5 \times 10^{-4}$ mol), 50 microliters of ligand (tetrafluorophenyl 4,5-di-(tetrahydropyranylmercapto-acetamido)pentanoate (0.40 milligrams; $6.5 \times 10^{-7}$ mol), 50 microliters of stannous chloride (0.5 milligrams, $2.6 \times 10^{-6}$ mol), and 50 microliters of I-125 in acetonitrile (4.25 micrograms, $2.3 \times 10^{-8}$ mol). The mixture is heated at 50° C. for one hour and then 0.30 milliliters of 1N NaOH is added.

The tetrafluorophenyl ester product of the I-125 $N_2S_2$ complex is purified on a $C_{18}$ Baker-10 SPE column. After application to the column, impurities are washed off with $2 \times 3$ milliliters of water and $4 \times 3$ milliliters of 10% $CH_3OH/0.01M$ phosphate, pH 7. The product is eluted with 2 milliliters of acetonitrile and then the solution is reduced to dryness under a stream of nitrogen.

Conjugation of the I-125 $N_2S_2$ complex is done by addition of the antibody of Example VIII or Example IX to the complex in borate buffer (0.5M, pH 9). Incubation is maintained for 30 minutes at room temperature.

EXAMPLE XI

Antibody-Label Conjugations

A Tc-99m chelate is conjugated to the monoclonal antibody of Example VIII or Example IX as follows. 75 mCi of Tc-99m chelated by N, N'-bismercaptoacetyl 4,5-diaminopentanoic acid is prepared by dithionite reduction of Tc-99m pertechnetate at basic pH with 25 micrograms of the $N_2S_2$ ligand. The acid is activated by adding the above complex at pH 7 in 0.5 ml water to 100 microliters of water:acetonitrile (1:9) containing 3.0 milligrams of 2,3,5,6-tetrafluorophenol and 100 microliters of water:acetonitrile (1:9) containing 7.5 milligrams of 1-cyclohexyl-3-(2-morpholinoethyl)carbodiimide (morpho CDI). After storing for 18 hours at room temperature, the mixture is purified using a Baker-10 SPE reversed phase $C_{18}$ column. The column is conditioned with 2 milliliters of ethanol and is then washed with HPLC grade water. The reaction mixture is then added to the column, the column is then washed four times with 2 milliliter volumes of 10% methanol in 0.01 sodium phosphate, pH 7.0 and the ester complex is finally eluted with 2.5 milliliter portions of acetonitrile.

To a 2 milliliter vial is added 4.5 mCi of activated ester complex in acetonitrile, the solvent is evaporated in a nitrogen stream, and 0.4 milliliters of sodium borate (0.5 M, pH 9.0) is added. While agitating, the antibody is added and incubation at room temperature is conducted for 30 minutes.

EXAMPLE XII

Method of Imaging—Monoclonal Antibody as Recognition Agent 30 mCi of the labeled monoclonal antibody of EXAMPLE XI is admixed with a pharmaceutically acceptable saline solution. This mixture is administered intraperitoneally to the patient. After 18 hours, a diagnostic image is prepared through the use of a STARCAM gamma camera made by General Electric Corporation.

EXAMPLE XIII

Method of Imaging—Dual (Cold and Hot) Monoclonal Antibody Administration 10 mg of non-labeled monoclonal antibody of EXAMPLE VIII is admixed with a pharmaceutically acceptable saline solution. This mixture is administered intravenously to the patient thirty minutes prior to radiolabeled antibody. 30 mCi of the labeled monoclonal antibody of EXAMPLE X is admixed with a pharmaceutically acceptable saline solution and administered to the patient intravenously. Following the passage of 3–8 additional hours, a diagnostic image is prepared through the use of a STARCAM gamma camera made by General Electric Corporation.

EXAMPLE XIV

Method of Imaging—Monoclonal Antibody as Recognition Agent 20 mCi of the labeled monoclonal antibody of EXAMPLE XI is admixed with a pharmaceutically acceptable saline solution. This mixture is administered intravenously to the patient. After 24 hours, a diagnostic image is prepared through the use of a Raytheon LFOV Anger gamma camera. A diagnostician examines the prepared image and determines whether the image is characteristic of tissue having damage mediated by inflammation.

EXAMPLE XV

Method of Imaging—Dual (Cold and Hot) Monoclonal Antibody Administration 7.5 milligrams of non-labeled monoclonal antibody of EXAMPLE IX is admixed with a pharmaceutically acceptable saline solution. This mixture is administered intravenously to the patient. 5 minutes later, 0.5 milligrams of the labeled monoclonal antibody of EXAM- PLE XI is admixed with a pharmaceutically acceptable saline solution and administered to the patient subcutaneously. Following the passage of 12 additional hours, a diagnostic image is prepared through the use of Raytheon LFOV Anger gamma camera. A diagnostician examines the prepared image and determines whether the image is characteristic of tissue having damage resulting from a transient decrease in blood flow to that tissue.

EXAMPLE XVI

Diagnostic Kit

Lyophilized recognition agent of EXAMPLE VIII is contained in a sterile vial. A buffer of pharmaceutically acceptable solution is contained in an another sterile vial. Both vials are contained in a box. Instructions regarding the labeling and use of the recognition agent are printed on a label affixed to the box by an adhesive.

EXAMPLE XVII

Diagnostic Kit—Dual Administration Method

Lyophilized recognition agent of EXAMPLE VIII is contained in two sterile vials. Pharmaceutically acceptable solution is contained in a third sterile vial. All three vials are housed in a box in which the instructions for the use of the kit are contained in a separate pamphlet.

EXAMPLE XVIII

Monitoring Method

During steroid treatment of inflammation, diagnostic images are prepared as in EXAMPLE XIV at 72 hour intervals. The series of images is examined to determine the fate of the damaged tissue over time. An observed decrease in the amount of labeled recognition agent in the area of tissue damage over time indicates treatment success.

EXAMPLE XIX

Monitoring Method

During the course of treatment of cardiac ischemia, diagnostic images are prepared as in Example XV at 72 hour intervals. The series of images is examined to determine the fate of the damaged tissue over time. An observed increase in the amount of labeled recognition agent in the area of tissue damage over time indicates treatment failure and a danger of myocardial infarction.

EXAMPLE XX

Activation of Polymorphonuclear Leukocytes

Cytophoresis is performed on a patient, in order to obtain from peripheral blood a fraction enriched for mature PMNs. Briefly, the PMN enrichment technique involves standard blood phoresis performed in combination with hydroxyethyl starch, a sedimenting agent. The patient may also be pretreated with prednisone for 12 to 13 hours immediately preceding the phoresis process. Prednisone is a steroid that induces release of mature neutrophils from the bone marrow to the peripheral blood. The PMNs are collected under sterile conditions, with a typical cellular recovery approximating $30 \times 10^9$ cells/cytophoresis process.

The harvested PMNs are incubated for 15 to 30 minutes with 100 U/ml GM-CSF (recombinant human GM-CSF may be obtained from a COS cell transfectant (D. Metcalf et al., Blood 67:37-45, 1986) in order to generate activated PMNs.

EXAMPLE XXI

Activation of Macrophages

Peripheral blood from patients is obtained via venipuncture and fractionated by density centrifugation. That is, heparinized blood is layered onto Ficoll-Pague (Pharmacia), the gradient is centrifuged and the mononuclear cells are harvested from the plasma-gradient interface. The harvested cells are washed twice in serum-free RPMI 1640 medium. Monocytes are collected by adhering interface cells in RPMI 1640 containing 10% fetal calf serum and penicillin/streptomycin at $5 \times 10^6$ cells/milliliter. Adherent monocytes are incubated in the presence of a low pyrogen content M-CSF preparation (20 nanograms/milliliter, Genetics Institute) for 72 hours.

EXAMPLE XXII

Activated Autologous PMN/Labeled I-CAM Interaction Inhibitor Conjugate

Fab fragments of 4F-2 [an anti-human monocyte antibody produced by the hybridoma cell line designated "4F2C13", ATCC, Rockville, Md.] capable of blocking LFA/I-CAM interaction are radiolabeled in accordance with the procedure described in European Patent Application Publication No. 0188256. Activated PMNs prepared in accordance with Example XX are incubated with these radiolabeled antibody fragments for 60 minutes. Conjugates formed from this incubation are then infused into a patient.

Additional radiolabeled antibody fragments are infused into a patient together with the conjugates prepared above. A diagnostic image is then prepared through the use of a STARCAM gamma camera made by General Electric Corporation.

What is claimed is:

1. A method of imaging tissue sites of inflammation comprising:
   (1) radiolabeling a recognition agent, wherein said agent is a chemotactic peptide, an eosinophilotactic peptide or wherein the agent is capable of interacting selectively with a chemotactic peptide receptor associated with activated leukocytes accumulated at said tissue site;
   (2) infusing radiolabeled recognition agent into a patient; and
   (3) imaging said tissue sites, whereby medical conditions involving tissue damage mediated by inflammation may be detected, evaluated or monitored.

2. A method of claim 1, wherein the recognition agent is radiolabeled with $^{111}$In.

3. A method of claim 1, wherein said chemotactic peptide receptor is a receptor for f-met-leu-phe.

4. A method of claim 1, wherein said chemotactic peptide is f-met-leu-phe.

5. A method of claim 1, wherein said chemotactic peptide is radiolabeled via an additional tyrosine, lysine, cysteine or phenylalanine residue synthesized as part of the peptide.

6. A method of claim 1, further comprising:
   (4) comparing inflammation site localization of said chemotactic peptide and reticuloendothelial system localization of said peptide, wherein exhibition of a substantial affinity of said peptide for circulating or reticuloendothelial cells necessitates step (5); and, (5) altering the amino acid sequence of the peptide through addition or deletion of amino acids, so as to more closely correlate peptide structure with that bound by high affinity receptors of the activated leukocytes and less closely correlate with that bound by receptors of non-activated leukocytes, thereby producing a modified peptide capable of preferentially binding to activated leukocytes at sites of inflammation.

* * * * *